United States Patent [19]
Bauer et al.

[11] Patent Number: 5,488,951
[45] Date of Patent: Feb. 6, 1996

[54] EXTRACORPOREAL TREATMENT APPARATUS

[75] Inventors: Edgar Bauer, Kraichtal; Werner Krauss, Knittlingen; Dietmar Stettner, Mühlacker, all of Germany

[73] Assignee: Richard Wolf GmbH, Knittlingen, Germany

[21] Appl. No.: 156,604

[22] Filed: Nov. 23, 1993

[30] Foreign Application Priority Data

Jan. 14, 1993 [DE] Germany ............ 43 00 740.6

[51] Int. Cl.⁶ ...................................... A61B 6/00
[52] U.S. Cl. .................. 128/653.1; 601/2; 601/4; 607/97; 378/162; 378/175
[58] Field of Search ............... 128/653.1, 660.03; 601/2–4; 607/97; 378/195–197, 162, 175, 205

[56] References Cited

U.S. PATENT DOCUMENTS 5,230,329  7/1993  Puppo ........................... 601/4
5,388,581  2/1995  Bauer et al. .................... 601/4

FOREIGN PATENT DOCUMENTS 0397980  11/1990  European Pat. Off. ......... 601/4
0396866  11/1990  Germany.
0402584  12/1990  Germany.
0538659   4/1993  Germany.

*Primary Examiner*—Ruth S. Smith
*Attorney, Agent, or Firm*—Panitch Schwarze Jacobs & Nadel

[57] ABSTRACT

The extracorporeal treatment apparatus has an electroacoustic transducer for producing focused sound waves and a patient support which can be moved with respect to the transducer for the purpose of positioning a patient. The transducer is arranged pivotably about its focus with respect to the patient support. The treatment apparatus is provided to connect an external X-ray location device essentially comprising an X-ray source, an X-ray image-receiver and a support frame connecting these components. Mechanical coupling between the X-ray location device and the transducer of the treatment apparatus takes place such that the X-ray location devices may follow the pivoting movements of the transducer.

11 Claims, 9 Drawing Sheets

EXTRACORPOREAL TREATMENT APPARATUS

BACKGROUND OF THE INVENTION (a) Field of the Invention

The invention relates to an extracorporeal treatment apparatus having an electroacoustic transducer for producing focused sound waves and having a patient support which can be moved with respect to the transducer for the purpose of positioning a patient, the transducer of which being arranged pivotably about its focus with respect to the patient support.

Treatment apparatus of this type are used for example in the destruction of concretions or in the treatment of tissue (tumor treatment). They usually operate using high-energy ultrasound, whether in the form of shock waves or in continuous or intermittent operation.

(b) Description of the Prior Art

A generic apparatus is known from German Offenlegungsschrift 3 916 093. The lithotripter described there has a dome-shaped transducer with ultrasound location device integrated therein and X-ray location device. Transducers and location devices are firmly connected to one another and may be pivoted about a confocal axis with respect to the patient support. Since the focus remains unchanged when pivoting the transducer and its location devices, the direction of the sound waves may be changed without altering the position of the patient, and this is a considerable advantage. Hence, for example obstructions in the sound path may be avoided. This also offers particular advantages for location, since the focus region within the patient body may be observed from different directions and viewing angles, as a result of which exact data on the spatial extension of any concretions or tissue areas to be treated may be obtained.

The comparatively high purchase price is regarded as disadvantageous for treatment apparatus of this type equipped with X-ray and ultrasound location. For application which becomes ever more varied both for treatment apparatus and for the location devices, attempts are made to separate them from each other at least for some of the time in order to be able to use them independently of one another and hence to increase the economic viability.

Hence the ultrasound location device often suffices for numerous applications in the aforementioned lithotripters. Treatment apparatus are therefore already known, in which a separate X-ray location device must be attached to the treatment apparatus if X-ray location is required. A commercially available X-ray C arc may then be used here. However, the prerequisite is that the treatment apparatus is designed so that enough space for inserting this C arc still remains.

Such an application for extracorporeal treatment apparatus in conjunction with an external X-ray location device is described, for example in European application 0 402 584. There it is essentially the problem of spatial arrangement between X-ray location device and the focus of the electroacoustic transducer which is usually posed for arrangements of this type. This problem is solved by a type of target device which is attached to the transducer and by means of which the X-ray arc is aligned with the focus in two positions. The adjusting operations required for this are not only time-consuming, but are also a burden to the patient because of the X-ray radiation thus occurring. A further disadvantage can be seen in that every time the position of the transducer is altered with respect to the patient, if for example certain regions of the body are shaded and are therefore not accessible from one side, the X-ray location device must always be realigned.

Starting from the state of the art mentioned in the introduction according to German Offenlegungsschrift 3 916 093, the object of the present invention is to design a generic treatment apparatus so that the X-ray location device may on the one hand be separated from the treatment apparatus, but on the other hand may be connected to and aligned with the latter quickly and simply while avoiding the aforementioned disadvantages.

SUMMARY OF THE INVENTION

This is achieved according to the invention in that an external X-ray location device, which essentially comprises an X-ray source, an X-ray image-receiving device and a support frame connecting these parts, hence forms a conventional X-ray C arc which can be coupled to the transducer such that during the pivoting movements of the transducer the X-ray location device follows these pivoting movements and hence remains assigned to the system without renewed fitting or aligning operations.

The design of the invention has the advantage that the known advantages for treatment apparatus with rigidly assigned X-ray location devices, as are known for example from German Offenlegungsschrift 3 916 093, are essentially retained—the pivoting movability of the transducer should be emphasised particularly here—but the known disadvantages which are associated with external X-ray location devices of the known type can essentially be avoided. The coupling required to connect the X-ray location device to the treatment apparatus can, as far as the X-ray location device is concerned, be easily retrofitted so that the commercially available X-ray C arcs may be used. These can be moved in any case and in most cases can also be adjusted at the height of its pivoting axis, so that the pivoting axis of the X-ray location device and of the transducer may be aligned at least essentially by means of manual alignment.

However, there is no problem if these axes are not flush with one another but slightly out of alignment. Suitable additional devices, by means of which exact assignment of the X-ray location device to the focus of the transducer is ensured in simple and very practicable manner, are provided for this in a development of the invention, and that is over the entire pivoting range of the transducer. After fitting and attaching the X-ray location device, this arrangement is maintained until the apparatus are separated from one another again.

These additional devices comprise firstly a spot film marker for the X-ray location device, which can be introduced into the focus of the transducer, and a control assigned to the X-ray location device which in conjunction with a position transmitter assigned to the transducer recognizes the particular transducer position and hence also pivoting position of the X-ray location device, and hence assigns the focus position with regard to the X-ray location device using a previously determined displacement curve. To determine this displacement curve it is only necessary to determine the position of the focus with the aid of the spot film marker in two pivoting positions, preferably the end positions, with the aid of the X-ray location device, from which the control device determines this curve or the corresponding values and takes it into account when representing the electronic spot film marker on the monitor.

The spot film marker for the X-ray location device is advantageously already provided on the treatment apparatus, particularly the transducer, so that it only has to be brought into the focus position as required. This may advantageously take place in that a telescope device which can be driven in and out is provided within the transducer or near the transducer, this spot film marker sitting on the ends of the telescope device so that the spot film marker lies in the focus of the transducer when the telescope is driven out and impedes neither treatment nor location when the telescope is driven in.

This may also be advantageously provided by introducing the spot film marker on the patient-side end of the ultrasound scanner. An advantageous device for pivoting this spot film marker out or in on the ultrasound scanner is described further below using an exemplary embodiment.

However, the spot film marker may also be introduced on the coupling membrane terminating the apparatus-side approach path to the patient, by adhering an appropriate X-ray positive marker there. In order to also ensure that this marker is actually arranged in the focus of the transducer, an optical device is advantageously provided which comprises, for example two lasers arranged within the transducer, the beams of which intersect in the focus of the transducer. If the two light spots forming on the membrane are aligned by displacing the membrane, the appropriate position of the membrane is situated in the focus of the transducer. An X-ray positive spot film marker may then be adhered at this point.

The commercially available X-ray C arcs already mentioned have an X-ray source at one end of the C and an X-ray image amplifier at the other end, the signal of which is supplied to an image-reproducing device, usually a monitor. A spot film marker, which is aligned with the central beam of the X-ray source, can usually be displayed on this monitor. For arrangements according to the state of the art it is always so that this central beam and hence the spot film marker fixed in the monitor has to be aligned with the transducer focus. Such millimeter-precise positioning is very time-consuming. The solution of the invention on the other hand only provides manual coarse alignment and in an advantageous embodiment has the possibility of tracking the electronic spot film marker on the spot film marker actually represented. It is thus possible without exact alignment of the X-ray location device to represent the focus of the transducer on the monitor, even if the actual spot film marker is not situated in the region of the central beam.

In order to ensure this even with the required precision in each pivoting position of the transducer and the X-ray location device, a control device is provided according to the invention which tracks the electronic spot film marker in accordance with the particular pivoting position of the transducer, and in particular on a path previously determined using the actual focus position in the pivoting end positions.

In order to have to make as few constructional changes as possible to the X-ray location device, it is advantageous not to record the pivoting position of the X-ray location device, but that of the transducer within the treatment apparatus and to supply it to the control device. Such recording may take place by means of a displacement transducer provided on the transducer. Displacement transducers within the scope of the invention is a sensor which records the position of the transducer, whether it be by displacement measurement, by angle measurement or in another manner.

It is advantageous if the coupling device, which fixes the X-ray location device on the treatment apparatus, is arranged near the transducer on the treatment apparatus-side and on the support frame on sides of the X-ray location device, and in particular near the X-ray source. Connection is thus achieved via short levers and in addition a very precise arrangement between X-ray source and transducer is guaranteed. It is advantageous if a window for the X-ray source is provided within the transducer dome, particularly for a transducer designed to be dome-shaped and constructed from piezoelectric elements.

In addition to the suitable design, the invention also indicates a process which is simple and quick to carry out for fitting an external X-ray location device to such a treatment apparatus, by means of which an arrangement between transducer focus and X-ray location device takes place according to the particular pivoting position. After attaching the X-ray location device to the transducer of the treatment apparatus, hence after mechanical connection of the units, the transducer is pivoted together with X-ray location device into one end position. The spot film marker for X-ray location, that is an X-ray positive marker, is then brought into the focus of the transducer (this may of course also take place at any previous time). The spot film marker is represented on the image-reproducing device by means of the X-ray location device, and the position of this spot film marker is stored in a control device. The transducer is then pivoted together with the X-ray location device into its other end position and again the position of the spot film marker represented is stored. The fitting is completed after the spot film marker has been removed from the focus. The control device then calculates a path which indicates the position of the transducer focus as a function of the pivoting position of the transducer. The electronic spot film marker provided in the image-reproducing device is tracked using this path parameter, so that the electronic spot film marker of the X-ray location device always corresponds to the actual focus position of the transducer with high precision.

BRIEF DESCRIPTION OF THE DRAWINGS

The foregoing summary of the invention, as well as the following detailed description of the preferred embodiments, will be better understood when read in conjunction with the appended drawings. For the purposes of illustrating the invention, there are shown in the drawings embodiments which are presently preferred, it being understood, however, that the invention is not limited to the specific arrangements and instrumentalities disclosed.

DETAILED DESCRIPTION OF PREFERRED EMBODIMENTS

Figure 1:
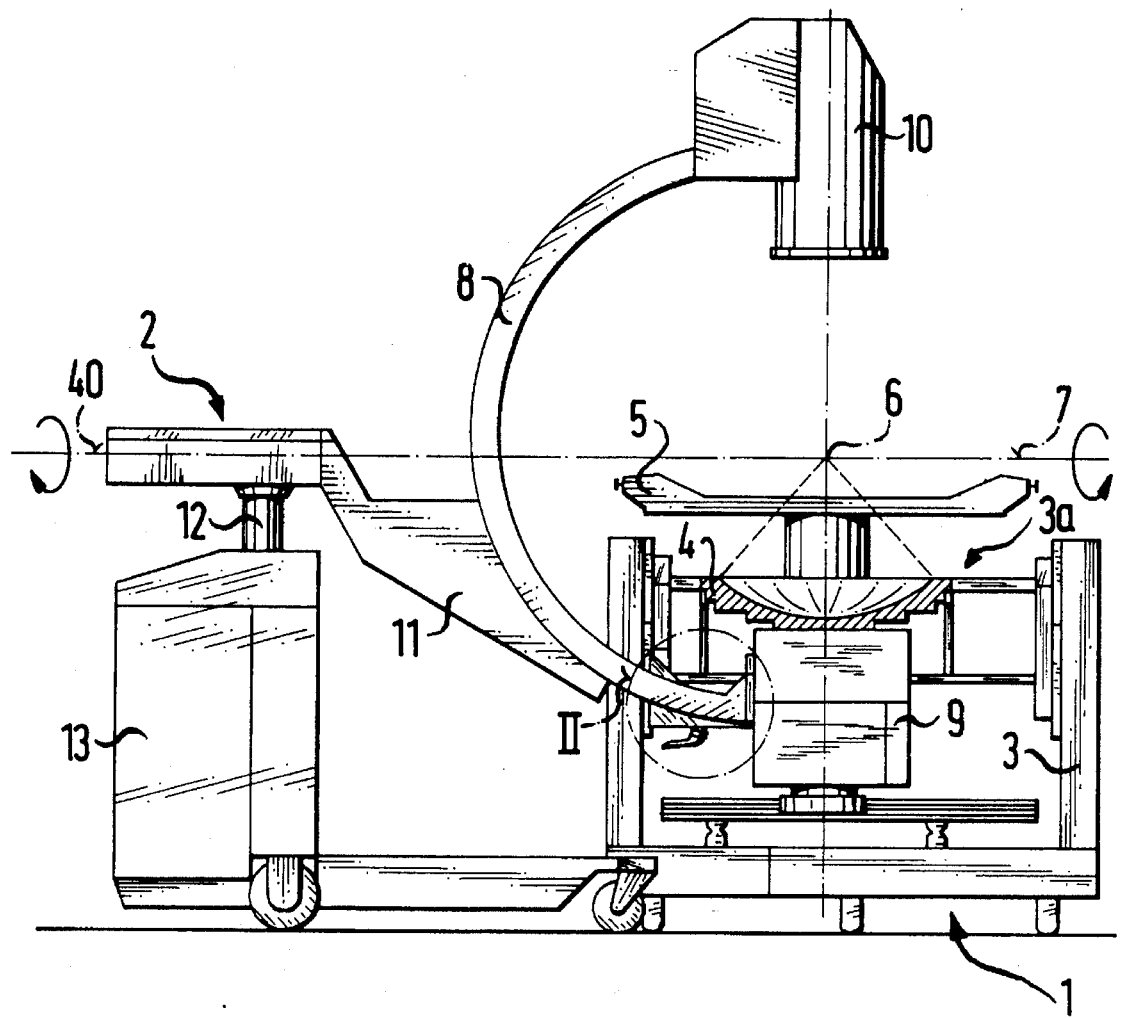
FIG. 1 shows a schematic representation of a treatment apparatus with attached X-ray location device in side view.

The arrangement according to FIG. 1 shows an extracorporeal treatment apparatus 1 with attached X-ray location device 2. The treatment apparatus 1 essentially comprises a support frame 3, in which an electroacoustic transducer 4 is pivotably mounted and to which a patient support 5 can be adjustably attached. The conventional peripheral units required, such as control electronics, adjusting devices and the like are not shown. The transducer 4 comprises a plurality of piezoelectric elements arranged like a dome, its focus is designated 6. The transducer 4 is mounted pivotably on a pivoting table 3a within the support frame 3 about the axis 7 in which the focus 6 lies. It may be pivoted out of the position shown vertical to the patient support 5 in each case by 15° to both sides. In order to position a patient situated on the patient support 5, the patient support 5 may be positioned in all three spatial coordinates with respect to the support frame 3 and to the transducer 4.

The X-ray location device 2 is designed as a commercially available X-ray C arc. The actual C arc 8 is part of the support frame. An X-ray source 9 is arranged at one end of this arc 8, an X-ray image amplifier 10 is arranged at the opposite side. The C arc 8 is designed as a profile and is guided in the direction of its arc on an arm 11, which is in turn connected to the undercarriage 13 by means of a stroke device 12 (not shown in detail). The arm 11 is mounted on the stroke device 12 so that the entire C arc can be pivoted with the arm 11 about the axis 40, which need not necessarily coincide exactly with the axis 7.

Figure 2:
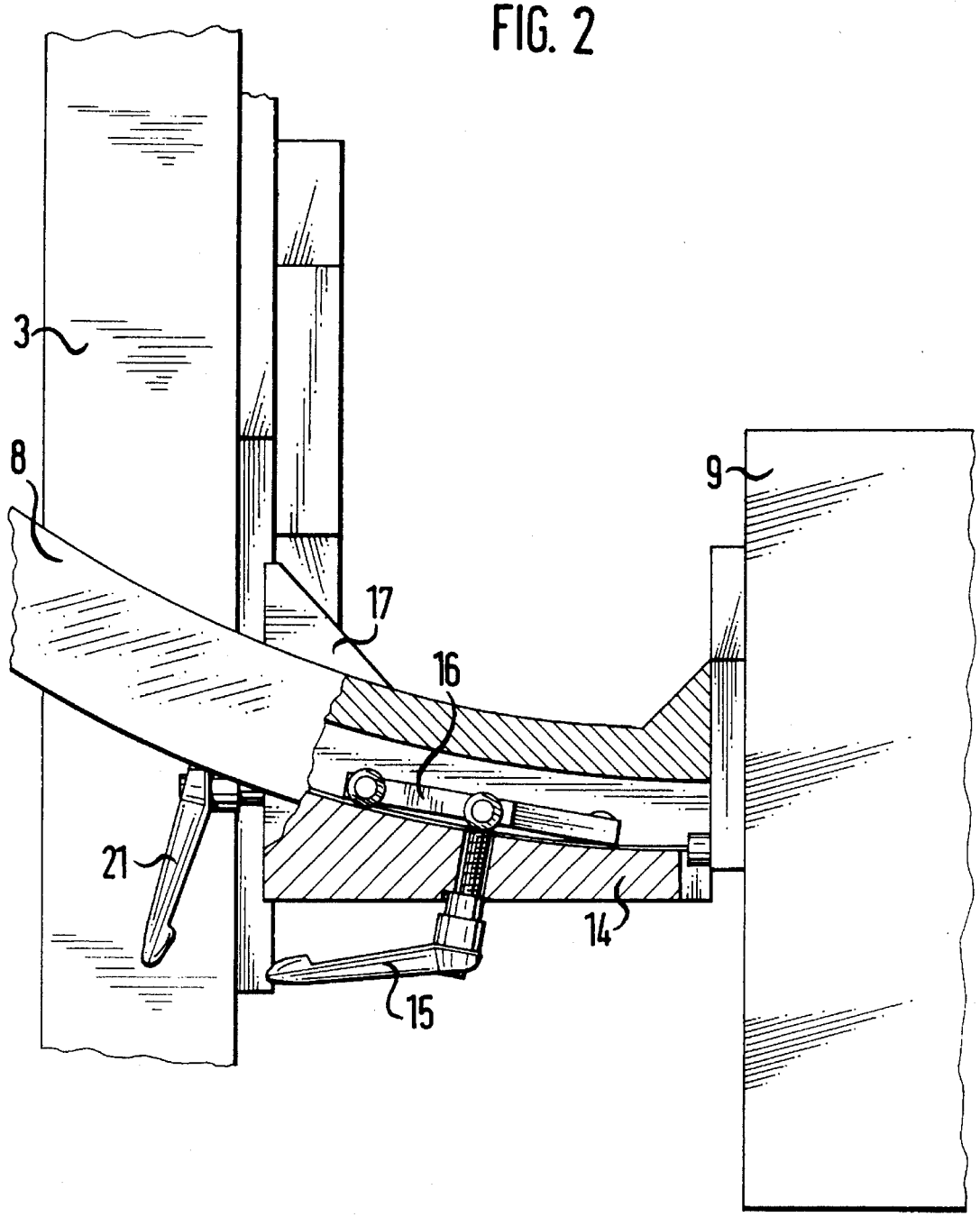
FIG. 2 shows the detail II in FIG. 1 in enlarged partial sectional representation.
Figure 3:
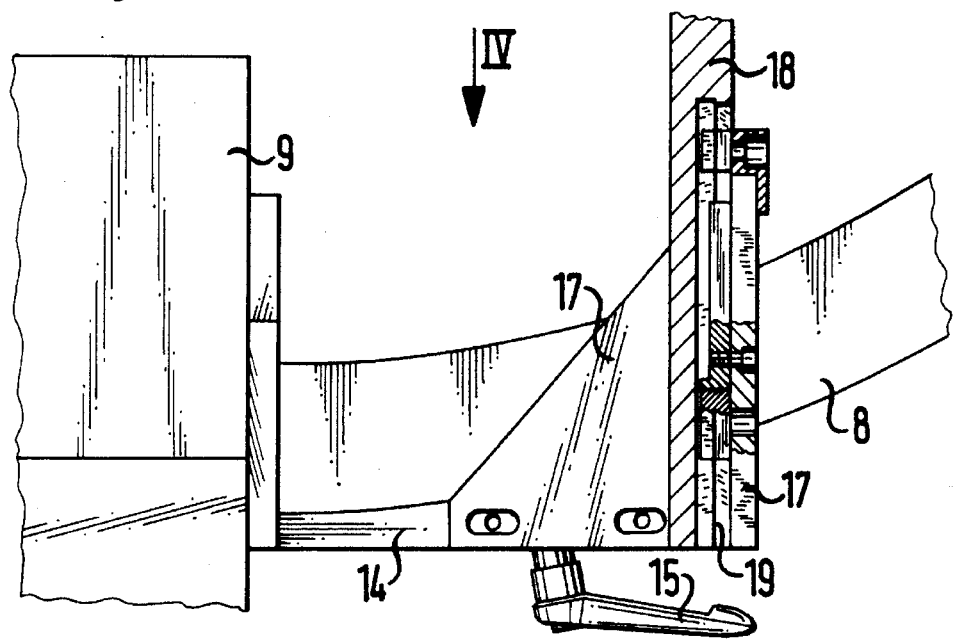
FIG. 3 shows a front view of the coupling region between treatment apparatus and X-ray location device from the rear side of FIG. 2.
Figure 4:
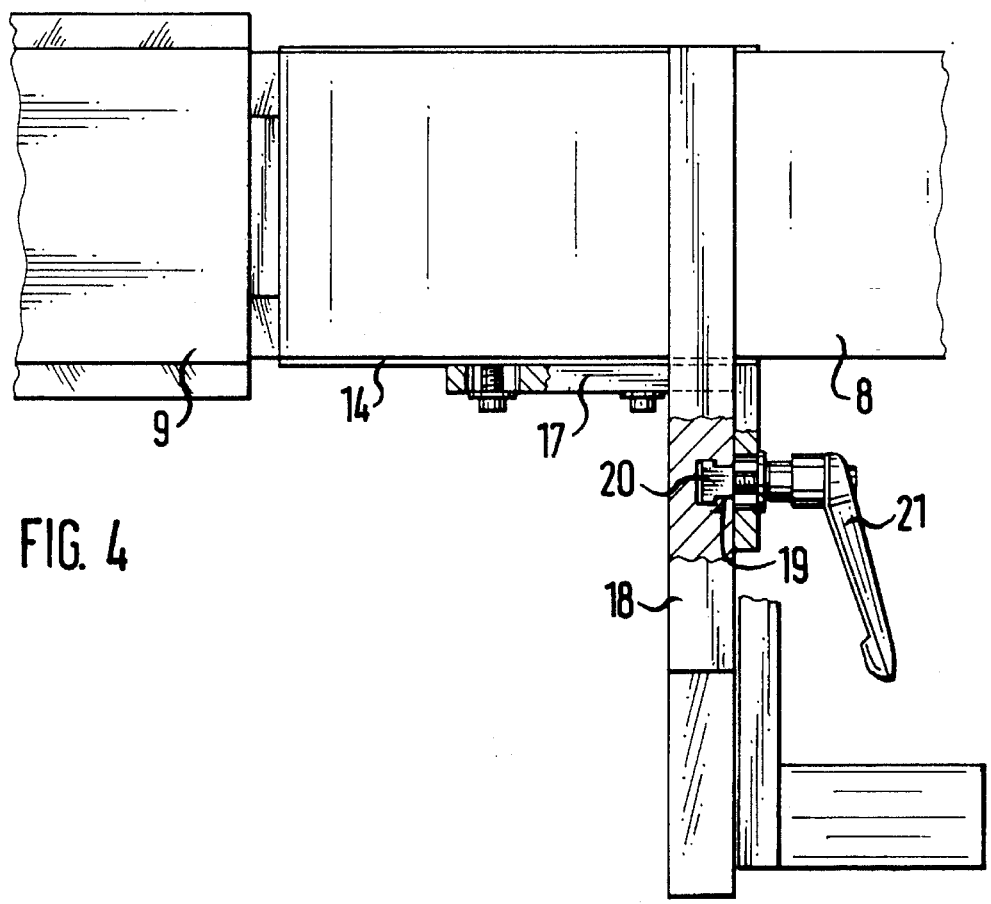
FIG. 4 shows a front view in the direction of the arrow IV in FIG. 3.

To connect the X-ray location device 2 to the treatment apparatus 1, the C arc 8 is first of all aligned by means of the stroke device 12 so that the axis 40 is approximately flush with the axis 7. The C arc is then pushed into the support frame 3 of the treatment apparatus 1 at its lower end supporting the X-ray source 9 until the X-ray source 9 is aligned with the X-ray window (not shown) provided in the transducer 4. The coupling shown in detail using FIGS. 2 to 4, which provides a firm mechanical connection between the apparatus, should then be terminated in this position.

The coupling comprises a C arc-side part and an apparatus-side part. A coupling body 14 is fixed near the X-ray source 9 on the C arc-side by means of the guide groove of the C arc open towards the outside and already present in the C arc 8. This coupling body 14 may be fixed by means of a lever 15, opposite a clamping plate 16 running within the groove. The coupling body 14 is essentially rectangular, but is adapted to the C arc 8 in the region of the latter, so that a large-surface area, secure surface is ensured. An angle plate 17, which is firmly screwed to the coupling body 14, is connected laterally to the coupling body 14. One limb of this angle plate 17 comes to rest against one flat side of the pivoting table 3a, and in particular against a clamping plate 18. This clamping plate 18 forms the apparatus-side part of the coupling. It has a groove 19 of T-shaped cross-section, into which engages an adjusting bolt 20 penetrating the corresponding limb of the angle plate 17 and which can be adjusted by means of a lever 21 acting externally on the angle plate, by means of which lever 21 the angle plate 17 can be firmly connected to the clamping plate 18. The actual coupling process thus takes place here between X-ray location device 2 and pivoting table 3a in the treatment apparatus 1. As a result of the large-surface area support surfaces of the coupling, the forces occurring here may safely be transferred, in particular it ensures that the C arc 8 follows the pivoting movements of the transducer 4.

Since the C arc-side part of the coupling is fixed while utilizing the existing profile, no constructional changes need to be made on the C arc itself. This part may be mounted quickly and simply on the C arc 8, optionally in situ.

As already mentioned in the introduction, only coarse alignment is carried out using this mechanical coupling between X-ray location device 2 and treatment apparatus 1, the exact fitting takes place by means of electronic tracking of the spot film marker on the monitor of the X-ray location device. For this fitting, the arrangement of an X-ray positive spot film marker 22 is required in the focus 6, which can then be shown by means of the X-ray location device 2. This spot film marker 22, for example in the form of a lead ball as shown in FIGS. 5 to 9, may be introduced in different ways.

Figure 5:
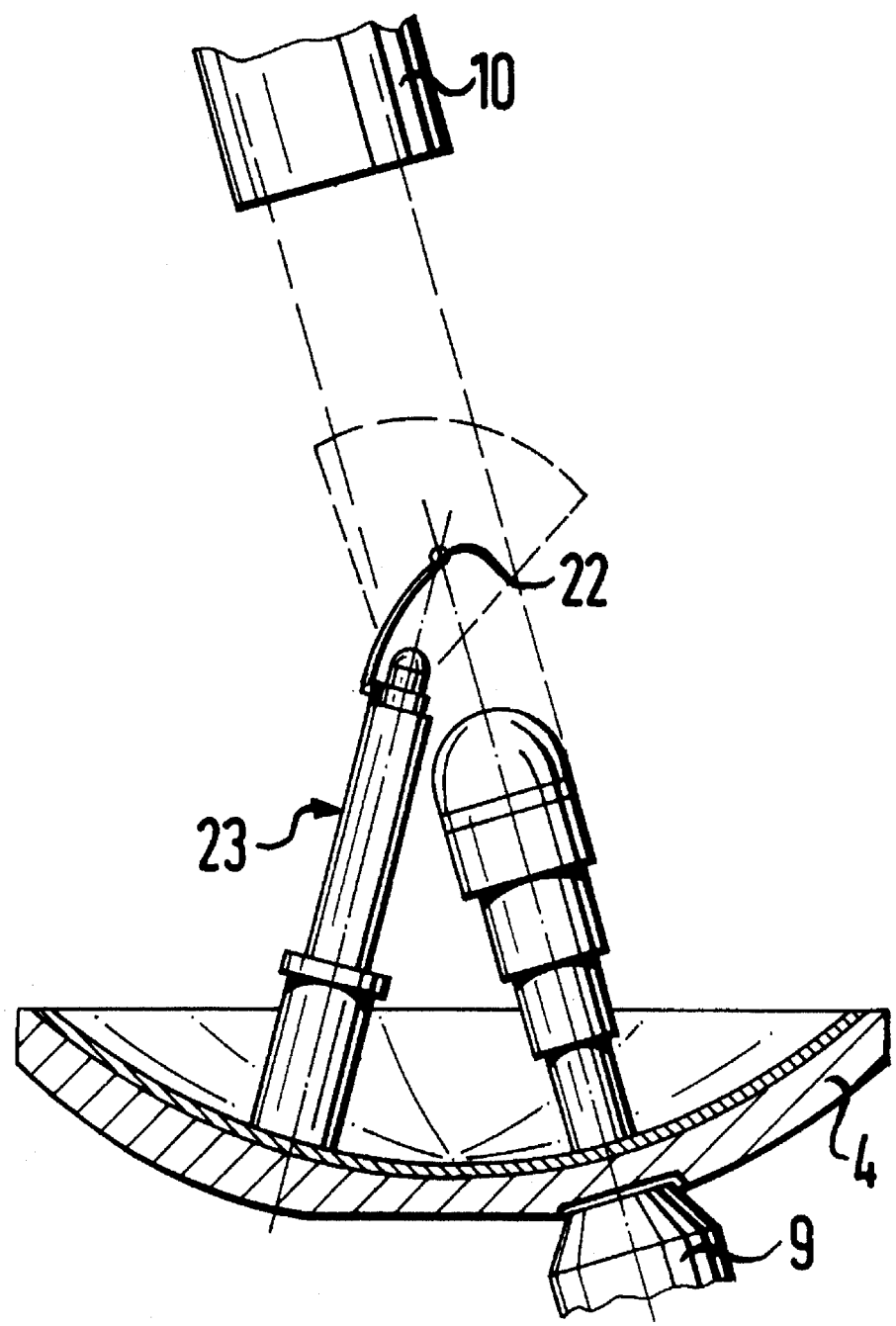
FIG. 5 shows the arrangement of a spot film marker on the ultrasound scanner.
Figure 6:
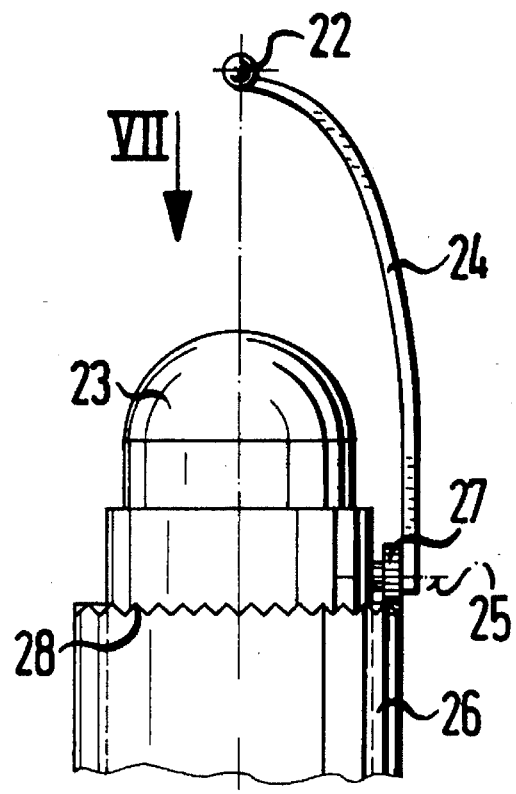
FIG. 6 shows an enlarged representation of the patient-side end of the ultrasound scanner with spot film marker.
Figure 7:
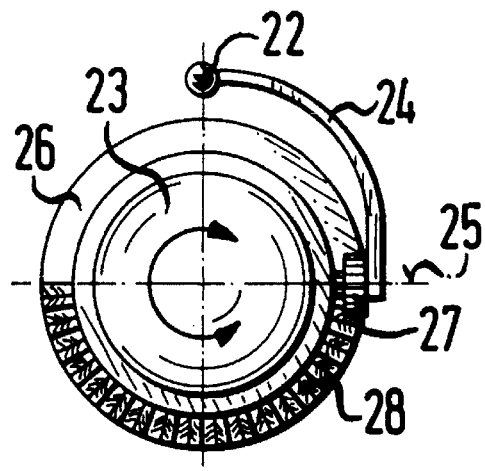
FIG. 7 shows a plan view in the direction of the arrow VII in FIG. 6 with spot film marker laterally pivoted away.

One embodiment is described using FIGS. 5 to 7, in which this spot film marker is arranged to pivot out on the patient-side end of an ultrasound scanner 23. The spot film marker 22 is retained by means of an arm 24, which is pivotably mounted on its scanner-side end with an axis 25 extending transversely to the longitudinal axis of the scanner, such that the spot film marker, as shown, can be pivoted into the focus or can be placed against the scanner 23. Pivoting takes place by rotating the scanner 23 within a fixed tube 26 surrounding the latter. An end-face toothed wheel 27, which meshes with a corresponding tooth system 28 disposed on the free end-face side of the tube 26, sits on the axis 25 and is firmly connected to the latter. The tooth system 28 extends, as can be seen in FIG. 7, only over a part of the end-face side, and in particular over an arc of about 180°. The toothed wheel 27 is rotated by rotating the scanner 23 within the tube 26, as a result of which the arm 24 with the spot film marker 22 pivots out or in, depending on the direction of rotation. The position representing the focus is determined by appropriate stops (not shown).

In order to be able to scan in different planes during ultrasound location, it is conventional to arrange the ultrasound scanner 23 to be rotatable. So that the spot film marker 22 is not unintentionally pivoted out during these rotary movements conventional during location, a part of the end-face side of the tube 26 has no teeth, so that only when the scanner 23 is rotated out over 180° to both sides does the spot film marker 22 pivot in.

Figure 8:
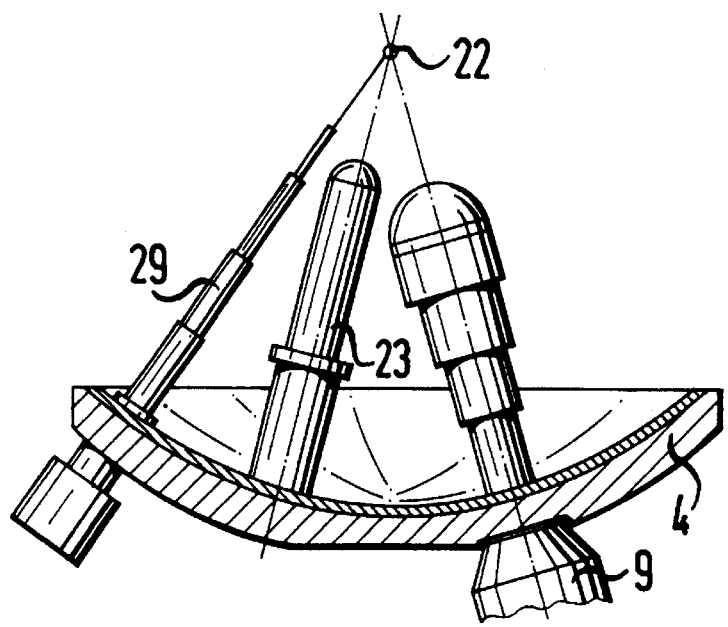
FIG. 8 shows further introduction of a spot film marker within the transducer.

An alternative device for introducing the spot film marker 22 is shown in FIG. 8. A telescope device 29, by means of which the spot film marker 22 can be positioned in the focus of the transducer by means of the telescope 29 which can be driven out, is provided there within the dome of the transducer 4. The telescope 29 may be actuated mechanically, pneumatically or hydraulically.

Figure 9:
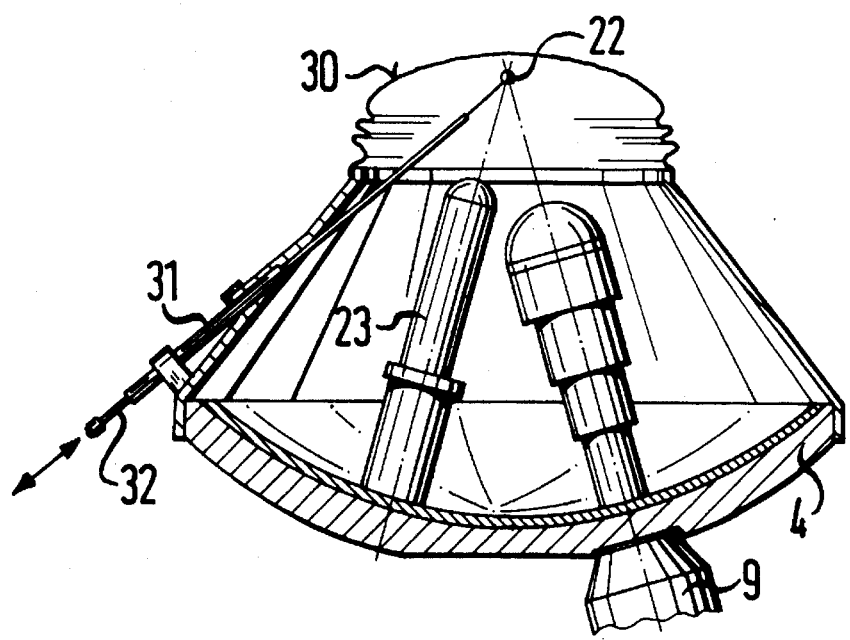
FIG. 9 shows a further embodiment for introducing a spot film marker.

In the embodiment according to FIG. 9, in which the transducer 4 is shown with its approach path filled with liquid and terminated by a membrane 30, the spot film marker 22 can be positioned in the focus 6 of the transducer by means of a guide tube 31 on a rod 32 arranged laterally of the transducer. The guide tube 31 is incorporated tightly into the approach path, the rod 32 is displaceable and mounted tightly within the guide tube 31. A stop is also provided here to reach the focus position quickly and safely. Moreover, the focus position of the spot film marker 22 can be additionally monitored by means of the ultrasound scanner 23.

Figure 10:
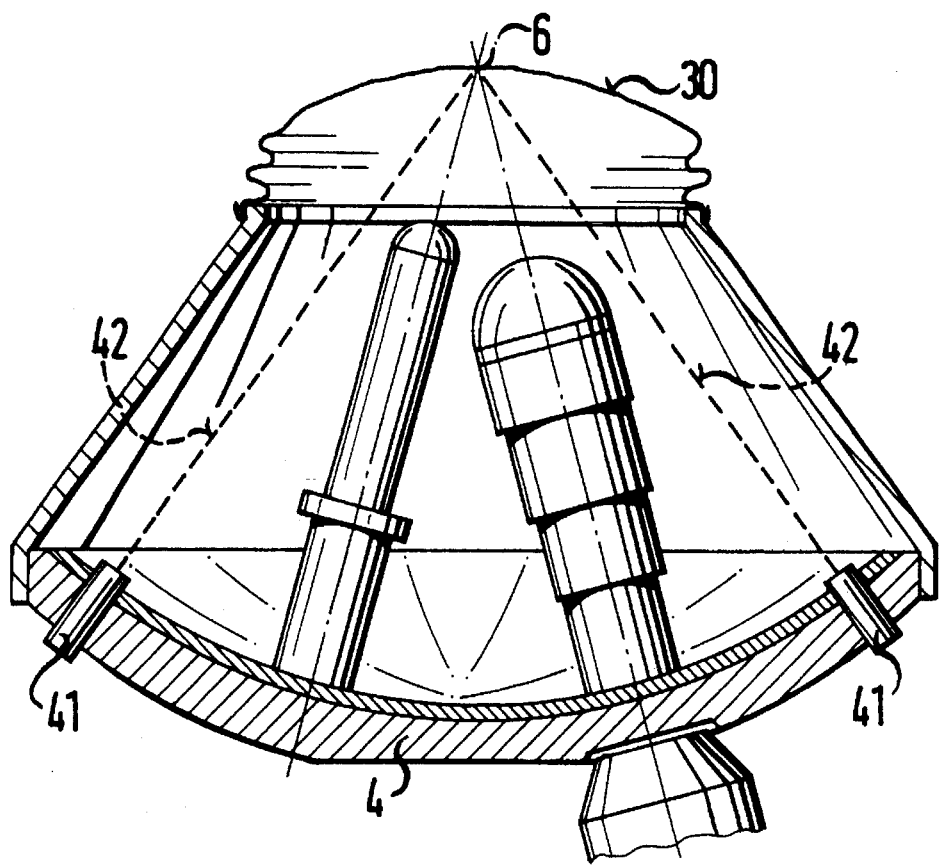
FIG. 10 shows an alternative device for arranging a spot film marker on the transducer.
Figure 11:
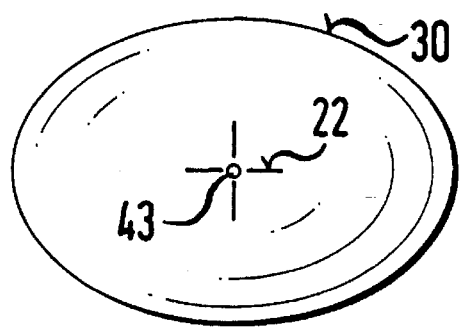
FIG. 11 shows a plan view of the coupling membrane of the transducer shown using FIG. 10.

An alternative device for introducing an X-ray positive spot film marker 22 is shown using FIGS. 10 and 11. Two He—Ne lasers 41, the light beam cluster 42 of which intersect in the focus 6 of transducer 4, are provided arranged approximately diametrally opposite within the transducer 4. To introduce the spot film marker 22, the distance of the coupling membrane 30 from the transducer 4 is then initially adjusted until the light spots 43 produced on the membrane 30 by the light beam cluster 42 are aligned, as shown in FIG. 11. An X-ray positive spot film marker 22, for example in the form of a metal cross, is then adhered to the membrane on the position of the light spots 43. Precise positioning of the spot film marker 22 in the focus 6 of the transducer 4 is thus ensured.

Figure 12:
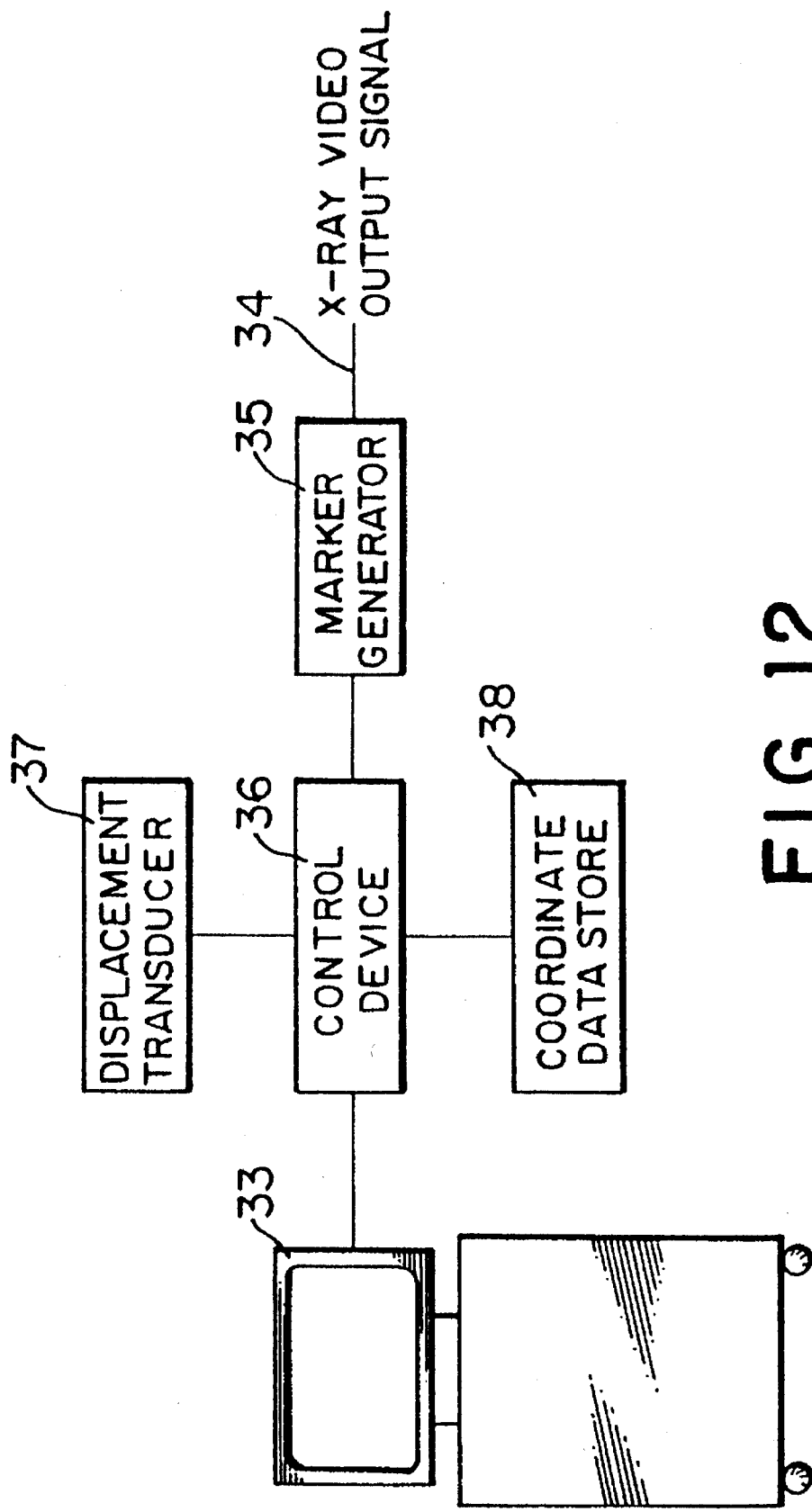
FIG. 12 shows the electronic coupling between transducer and X-ray location device on a block diagram.

Electronic correction described above is illustrated using FIG. 12 and ensures that the spot film marker shown on the monitor 33 always corresponds to the focus 6 of the transducer. The video output signal of the X-ray image amplifier 10 is designated 34 in FIG. 12. This signal then passes through a spot film marker generator 35 which generates an electronic spot film marker on the position of the monitor image. A control device 36, which receives a signal about the pivoting position of the transducer via a displacement transducer 37 arranged on the transducer and has access via a store 38 to data on the actual coordinates of the spot film marker 22 represented in the end positions of the transducer 4, is connected downstream of the spot film marker generator 35. The control device 36 calculates a path K using the coordinates filed in the store 38 on the actual focus position, on which path K the focus 6 moves when pivoting the transducer 4 about the axis 7 or when pivoting the X-ray C arc 8 with it about the axis 40. The particular deviations resulting therefrom are determined, the electronic spot film marker E produced by the generator 35 is tracked and shown on the monitor 33 on the position calculated corresponding to the focus 6. The values fixed in the store 38 are determined during fitting, as described in the introduction.

Figure 13A:
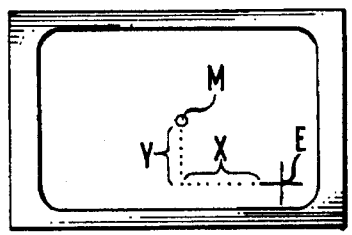
FIG. 13 shows the process steps during fitting using monitor displays.
Figure 13B:
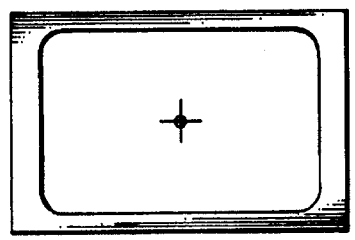
Figure 13C:
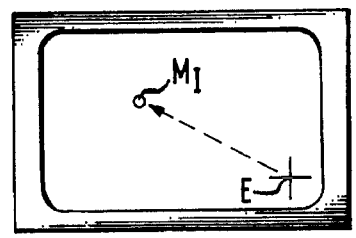
Figure 13D:
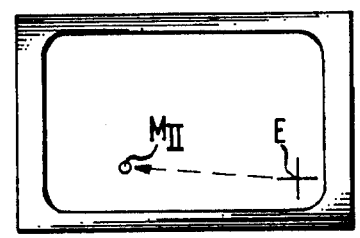
Figure 13E:
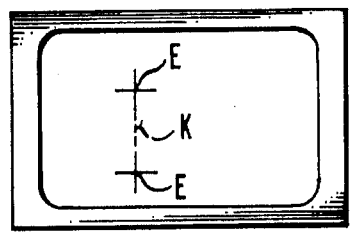

The fitting process is illustrated below using FIG. 13:

The principle of tracking the electronic marker on the spot film marker represented is first of all illustrated using FIGS. 13A and 13B. The spot film marker 22 represented is characterised by M, the electronic marker by E. In order to align these markers, as shown in FIG. 13B, the coordinates X and Y should be entered. Such input may be carried out by means of keys or even with the aid of an optical display apparatus. The coordinates X and Y in the two extreme positions of the transducer are stored in the store 38. These processes are shown using FIGS. 13C and 13D by way of example. It can thus be seen clearly that the actual representations of the spot film marker 22 have different positions in the two pivoting positions I and II. These deviations are achieved, for example in that the axes 40 and 7 are not exactly flush with one another. After the electronic spot film marker E is aligned with the actual spot film marker M represented in both pivoting positions and the corresponding displacement coordinates have been stored, a path K is calculated within the control device 36 which represents the position of the focus as a function of the pivoting movement with respect to the X-ray location device. The spot film marker E is shown on the monitor 33 using this path K in accordance with the particular pivoting position during later location.

The present invention may be embodied in other specific forms without departing from the spirit or essential attributes thereof and, accordingly, reference should be made to the appended claims rather than to the foregoing specification as indicating the scope of the invention.

We claim:

1. An extracorporeal treatment apparatus comprising an electroacoustic transducer for producing focused sound waves for treatment of a patient, a patient support and means for moving the support for positioning a patient with respect to the transducer, the transducer having a focus and means for pivoting the transducer about its focus with respect to the patient support, an external X-ray location device comprising an X-ray source, an X-ray image-receiving device and a support frame connecting them, said location device having means for supporting the location device independently of the transducer, means for releasably coupling the X-ray location device to the transducer such that the X-ray location device follows pivoting movements of the transducer, an actual spot film marker (M) positioned between the x-ray source and the x-ray image-receiving device, and an electronic spot film marker generator which generates an electronic spot film marker (E), wherein the X-ray image-receiving device has an electronic image-reproducing device for representing the electronic spot film marker (E), and means for tracking the electronic spot film marker (E) on the actual spot film marker (M).

2. The extracorporeal treatment apparatus according to claim 1, further comprising means for introducing the actual spot film marker into the focus of the transducer.

3. The extracorporeal treatment apparatus according to claim 2, wherein the spot film marker is positioned on a coupling membrane of the transducer, and means for placing the coupling membrane against the patient during treatment.

4. The extracorporeal treatment apparatus according to claim 3, further comprising two light sources arranged on the transducer and producing beams which intersect in the focus of the transducer for positioning the spot film marker on the coupling membrane.

5. The extracorporeal treatment apparatus according to claim 4, wherein said light sources are lasers.

6. The extracorporeal treatment apparatus according to claim 2, further comprising an ultrasound scanner arranged on the transducer, and wherein the means for introducing the spot film marker comprises means for pivoting the marker out toward an end of the ultrasound scanner nearest the patient.

7. The extracorporeal treatment apparatus according to claim 1, further comprising a telescope device, and wherein the actual spot film marker sits on the end of the telescope device, the telescope device being arranged in the transducer and having means for driving the actual spot film marker in and out of the focus.

8. The extracorporeal treatment apparatus according to claim 1, wherein said tracking means comprises an electronic control device electrically connected to the X-ray location device, said control device tracking the electronic spot film marker (E) on a previously calculated path (K) when the transducer and X-ray location device are pivoted together, and means for recording and transmitting to the control device a particular pivoting position of the transducer.

9. The extracorporeal treatment apparatus according to claim 1, further comprising a displacement transducer located on the electroacoustic transducer for measuring a pivoting position of the electroacoustic transducer.

10. The extracorporeal treatment according to claim 1, further comprising a transducer support, and wherein the coupling means is mounted on the support frame near the X-ray source and on the transducer support near the transducer.

11. The extracorporeal treatment apparatus according to claim 1, wherein the transducer comprises a dome-shaped arrangement of a plurality of piezoelectric elements, and the transducer has a window and an X-ray cone for the X-ray source located in the dome-shaped arrangement.

* * * * *